US006864109B2

(12) United States Patent
Chang et al.

(10) Patent No.: US 6,864,109 B2
(45) Date of Patent: Mar. 8, 2005

(54) METHOD AND SYSTEM FOR DETERMINING A COMPONENT CONCENTRATION OF AN INTEGRATED CIRCUIT FEATURE

(75) Inventors: Vincent S. Chang, Hsinchu (TW); Chi-Chun Chen, Kaohsiung (TW); Chun-Lin Wu, Hsinchu (TW); Tze-Liang Lee, Hsinchu (TW); Shih-Chang Chen, Hsinchu (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 0 days.

(21) Appl. No.: 10/625,410

(22) Filed: Jul. 23, 2003

(65) Prior Publication Data

US 2005/0019964 A1 Jan. 27, 2005

(51) Int. Cl.[7] .......................... H01L 21/26; H01L 21/66

(52) U.S. Cl. .......................... 438/16; 438/783; 438/786

(58) Field of Search .......................... 438/16, 5, 7, 783, 438/786

(56) References Cited

U.S. PATENT DOCUMENTS 6,362,085 B1 3/2002 Yu et al.
6,627,463 B1 * 9/2003 Sarfaty .......................... 438/7
6,669,782 B1 * 12/2003 Thakur ....................... 118/715

FOREIGN PATENT DOCUMENTS

WO WO-02-39097 A2 5/2002

* cited by examiner

*Primary Examiner*—Caridad Everhart
(74) *Attorney, Agent, or Firm*—Slater & Matsil, L.L.P.

(57) ABSTRACT

A method of determining a composition of an integrated circuit feature, including collecting intensity data representative of spectral wavelengths of radiant energy generated by a plasma during plasma nitridation of an integrated circuit feature disposed on a substrate, analysing the in intensity data to determine a peak intensity at one of the wavelengths, and determining a component concentration of the feature based on the peak intensity.

17 Claims, 6 Drawing Sheets

METHOD AND SYSTEM FOR DETERMINING A COMPONENT CONCENTRATION OF AN INTEGRATED CIRCUIT FEATURE

TECHNICAL FIELD

The present invention is directed, in general, to manufacturing integrated circuit devices and, more specifically, to methods and systems for determining a component concentration of an integrated circuit feature.

BACKGROUND

The basic metal-oxide-semiconductor field effect transistor (MOSFET) typically includes a gate oxide grown on a silicon substrate by thermal oxidation. Generally, the performance of the MOSFET is inversely proportional to the thickness of the gate oxide. Efforts to enhance performance and reduce power consumption have driven the thickness of the gate oxide to well below 100 Angstroms. However, such scaling introduces new problems into device fabrication and performance. For example, leakage currents may increase due to reduced gate oxide resistance to hot carrier injection. The rate of thermal oxidation can also be higher than practically manageable during formation of ultra-thin gate oxides.

Accordingly, manufacturers have begun incorporating nitrogen into gate oxides. For example, the surface of a silicon wafer may be enriched with nitrogen by implanting nitrogen atoms into the silicon surface to facilitate the growth of a nitrided oxide on the enriched wafer surface. Nitrogen may also be infused into the gate oxide by remote plasma nitridation. Such processes are introduced in U.S. Pat. No. 6,362,085 to Yu, et al., commonly assigned herewith, and incorporated in its entirety herein. This two step nitrogen enrichment process increases the dielectric constant of the gate oxide, not only decreasing its effective thickness with respect to gate capacitance, but also reducing leakage currents by increasing gate oxide resistance to hot carrier injection. In addition, because the initial silicon surface is nitrogen rich, the thermal oxidation rate is reduced, thereby improving process control by rendering the oxidation time and temperature more manageable.

Obviously, the nitrogen content of such nitrided oxides has significant impact on the subsequent processing and electrical performance of the resulting transistors. The detection of the nitrogen content of nitrided oxides typically employs secondary-ion mass spectroscopy (SIMS) or x-ray photoelectroscopy (XPS). However, SIMS is a destructive procedure, such that employing SIMS is limited to test and quality control wafers. Consequently, because SIMS is a destructive procedure and cannot be performed on production wafers, the determination of the nitrogen content of nitrided gate oxides formed on production wafers is relegated to speculation and estimates. Therefore, the true nitrogen content of nitrided gate oxides formed on production wafers may vary from design values due to uncontrolled process variations and fluctuations, possibly limiting their performance. Moreover, although XPS is non-destructive and can be used as an inline monitoring method, it is very expensive and requires air exposure, which can impact the electrical properties of the gate oxide being tested, particularly for ultra-thin oxides used in the 90-nm device technology and beyond.

Accordingly, what is needed in the art is a method for determining and monitoring nitrogen content of gate oxides that addresses the problems discussed above.

SUMMARY OF THE INVENTION

The present disclosure provides a method of determining a component concentration of an integrated circuit feature. In one embodiment, the method includes collecting intensity data representative of spectral wavelengths of radiant energy generated by a plasma during plasma nitridation of an integrated circuit feature disposed on a substrate, analyzing the intensity data to determine a peak intensity at one of the wavelengths, and determining a component concentration of the feature based on the peak intensity.

The present disclosure also provides a method of manufacturing a semiconductor device. In one embodiment, the method includes forming an integrated circuit feature on a substrate, nitriding the integrated circuit feature using a plasma, collecting intensity data representative of spectral wavelengths of optical energy emitted by the plasma during the nitriding, and analyzing the intensity data to determine a peak intensity at one of the wavelengths. A component concentration of the integrated circuit feature is estimated based on the peak intensity.

An etching system is also provided in the present disclosure. In one embodiment, the system includes a plasma chamber for containing a plasma, means for controlling a plasma nitridation process of a feature on a semiconductor substrate located within the chamber, and an optical sensor capable of detecting optical emissions from the plasma during the plasma nitridation process. The system also includes an optical spectral analyzer for analyzing the optical emissions detected by the sensor to determine a peak intensity of at least one emitted wavelength, and means for determining a component concentration of the feature based on the peak intensity.

The foregoing has outlined preferred and alternative features disclosed in the present disclosure so that those skilled in the art may better understand the detailed description that follows. Additional features will be described hereinafter that form the subject of the claims presented herein. Those skilled in the art should appreciate that they can readily use the present disclosure as a basis for designing or modifying other structures or processes for carrying out the same purposes and/or achieving the same advantages described in the present disclosure. Those skilled in the art should also realize that such equivalent constructions or processes do not depart from the spirit and scope of the present disclosure.

BRIEF DESCRIPTION OF THE DRAWINGS

The claims presented herein are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. Reference is now made to the following descriptions taken in conjunction with the accompanying drawings, in which:

DETAILED DESCRIPTION OF ILLUSTRATIVE EMBODIMENTS

Figure 1:
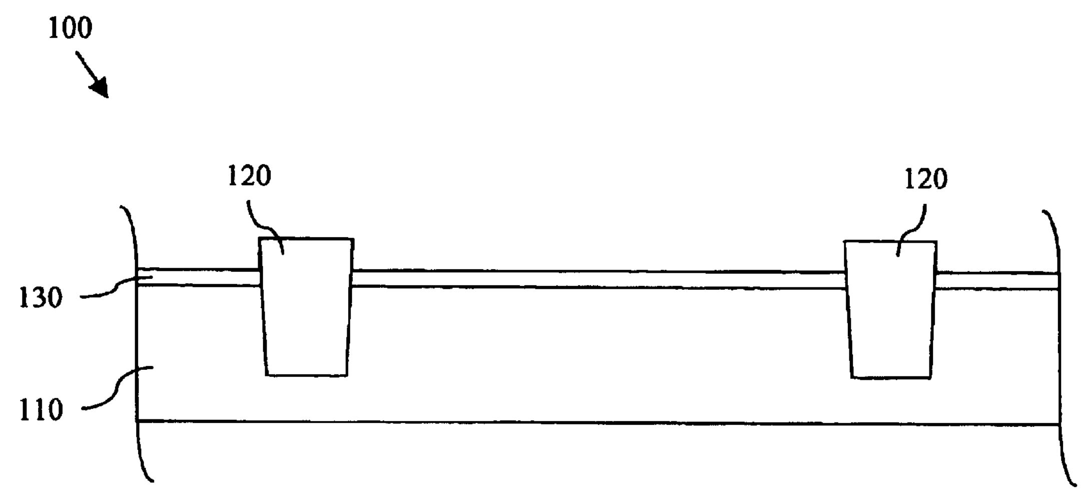
FIGS. 1 and 2 illustrate sectional views of one embodiment of a semiconductor device constructed according to the aspects of the present disclosure.

Referring initially to FIG. 1, illustrated is a sectional view of one embodiment of a semiconductor device 100 in an initial stage of manufacture according to aspects of the present disclosure. In the particular embodiment shown, the semiconductor device 100 is a metal-oxide-semiconductor field effect transistor (MOSFET). However, those skilled in the art will understand that the present disclosure may be readily adapted to other semiconductor devices.

The semiconductor device 100 includes a wafer 110, such as a p-type monocrystalline silicon wafer or another wafer (including a silicon on insulator (SOI) wafer) conventionally employed in the manufacture of semiconductor devices. Field oxides 120 may be formed in the wafer 110, such as by local oxidation of silicon (LOCOS) or by patterning trenches in the wafer 110 and filling the trenches with silicon oxide or another insulative material. In one embodiment, the field oxides 120 may be shallow-trench-isolation (STI) features, as known in the art.

A sacrificial silicon oxide layer 130 may then be thermally grown on the wafer 10. The sacrificial layer 130 may be grown at a temperature ranging between about 900° C. and about 1,000° C. in a dry oxygen ambient, and may have a thickness ranging between about 45 Angstroms and about 55 Angstroms. Of course, the present disclosure is not limited to methods employing the sacrificial layer 130 or other layers.

After forming the sacrificial oxide layer 130, the wafer 110 may be implanted with nitrogen ions ($N_2^+$). For example, nitrogen may be implanted at a dose ranging between about 1E14 atoms/$cm^2$ and about 1E15 atoms/$cm^2$ and an energy ranging between about 5 keV and about 10 keV. The sacrificial oxide 130 may serve as a screen oxide during the nitrogen implantation. The wafer 110 may then be annealed in a nitrogen ambient at a temperature ranging between about 1,000° C. and about 1,050° C. for a period ranging between about 10 seconds and about 30 seconds, such as by rapid-thermal-processing (RTP), to activate the implanted nitrogen near or at the interface between the wafer 110 and the sacrificial layer 130.

Figure 2:
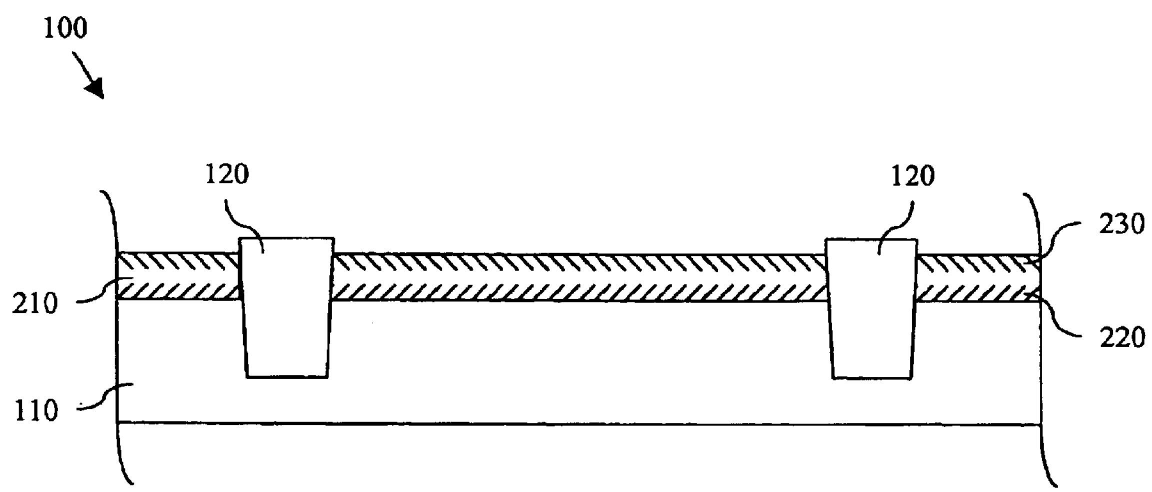

Referring to FIG. 2, illustrated is a sectional view of the semiconductor device 100 shown in FIG. 1 in a subsequent stage of manufacture according to aspects of the present disclosure. After the anneal step described above, the sacrificial layer 130 may be stripped and a gate oxide 210 may be grown on the wafer 110. The nitrogen rich layer exposed by the removal of the sacrificial layer 130 may be consumed by the gate oxide 210, such that the gate oxide 210 includes a nitrogen-rich region 220. As such, the gate oxide 210 may have a dielectric constant of at least about 4.0.

The gate oxide 210 may be grown to a thickness ranging between about 15 Angstroms and about 30 Angstroms at a temperature ranging between about 700° C. and about 900° C., in dry oxygen or other ambient. The oxidation time may range between about 30 seconds and about 60 seconds. The oxidation may be performed by in-situ steam generation (ISSG) or rapid thermal oxidation (RTO), although other processes may be employed. The reduction of the oxidation rate of the nitrogen rich silicon surface allows for greater process control, which may be advantageous for thermally growing ultra-thin gate oxides, wherein oxidation time and temperature may be much more manageable.

The wafer 110 may then be loaded into a remote plasma tool comprising a first chamber wherein a plasma is generated in a gas flow. The wafer 110 may be placed in a second chamber of the plasma tool located downstream from the first chamber so that species generated within the plasma pass over the wafer before being pumped out of the tool. In this manner, the gate oxide 210 is not directly exposed to the plasma and therefore does not suffer plasma damage. Of course, tools other than a dual chamber remote plasma tool may be employed within the scope of the present disclosure, including single chamber tools, as described below.

Nitrogen, $NH_3$ and/or other gases may be flowed into the plasma chamber at a flow rate ranging between about 600 SCCM and about 3,000 SCCM. The pumping rate of the plasma tool may be throttled to maintain a chamber pressure ranging between about 1 Torr and about 3 Torr in the second chamber. In this manner, the wafer 110 may be exposed to active nitrogen species from the remote plasma so that nitrogen may be incorporated into the gate oxide 210, thereby nitriding an upper portion 230 of the gate oxide 210. The remote plasma nitridation may be conducted with the wafer 110 heated to a temperature ranging between about 500° C. and 1,000° C., for a period ranging between about 3 minutes and about 5 minutes.

Nitriding the gate oxide 210 in this manner may further increase the dielectric constant of the gate oxide 210, possibly to about 6.0 or greater. With this increase in the dielectric constant, the effective "oxide" thickness of the nitrided gate oxide 210 may range between about 13 Angstroms and about 17 Angstroms, although the physical thickness of the gate oxide 210 may be about 20 Angstroms. Moreover, the gate oxide 210 may be nitrided by other conventional or future-developed means. Furthermore, a component other than nitrogen may be incorporated into the gate oxide 210 (or other integrated circuit feature) and be the subject of the component concentration detection processes disclosed herein.

The formation of the nitrided gate oxide 210 may be assisted by optical emission spectroscopy (OES). For example, OES may be employed prior to the formation of the nitrided gate oxide 210 to predict the nitridation parameters that will provide a desired nitrogen concentration within the gate oxide 210. OES may also be employed once the nitrided gate oxide 210 is substantially or completely formed to measure the resulting nitrogen content of the gate oxide 210. Furthermore, OES may be employed as an in-situ, real-time process during the formation of the nitrided gate oxide 210 to monitor the developing nitrogen concentration. For the purpose of clarity and brevity, the following discussion will be directed to an embodiment in which OES is employed to monitor the nitrogen content of the gate oxide 210 during formation of the nitrided gate oxide 210. Of course, those skilled in the art will recognize that the OES processes described herein may be readily adapted to determine, monitor and/or predict a concentration of a component other than nitrogen in an integrated circuit feature other than a gate oxide included in a device other than a MOSFET.

OES takes advantage of atoms that are excited to higher energy levels by collisions or by the absorption of radiation. Such atoms can de-excite by ejecting electrons or by emitting energy as photons. The photons have characteristic wavelengths which are the inverse of the energy emitted. The optical range of the wavelengths of interest in chemical analysis is typically about 100 nm to about 900 nm, from the extreme ultraviolet (UV) to the near infrared (IR).

Figure 3:
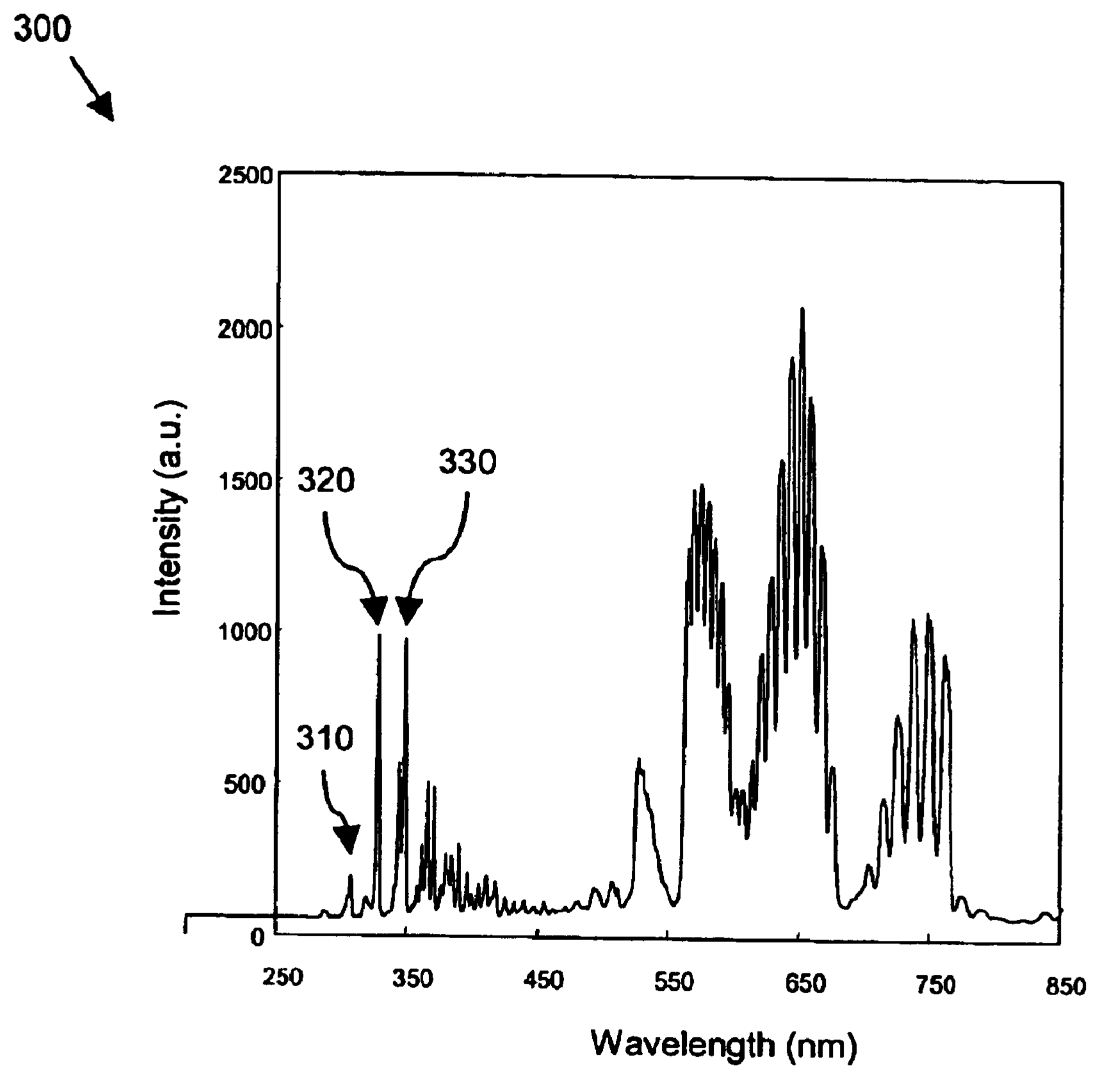
FIG. 3 illustrates a graph representative of intensities corresponding to wavelengths of optical emissions generated by a plasma in one embodiment of a semiconductor device manufacturing process according to aspects of the present disclosure.

During OES, optical emissions generated by the plasma during the plasma nitridation process are collected and analyzed to determine the intensities at each of the wavelengths that exist in the collected optical spectra. For example, referring to FIG. 3, illustrated is a graph 300 showing exemplary data resulting from the analysis of optical emissions collected from the plasma process wherein a gate oxide, such as the gate oxide 210 shown in FIG. 2, is nitrided. In the graph 300, the x-axis represents the wavelengths (nm) of the spectral emissions and the y-axis represents the intensity (arbitrary units) of each of the wavelengths. For example, a peak intensity 310 occurs at a wavelength of about 308 nm, another peak intensity 320 occurs at a wavelength of about 329 nm, and yet another peak intensity 330 occurs at a wavelength of about 349 nm.

Figure 4:
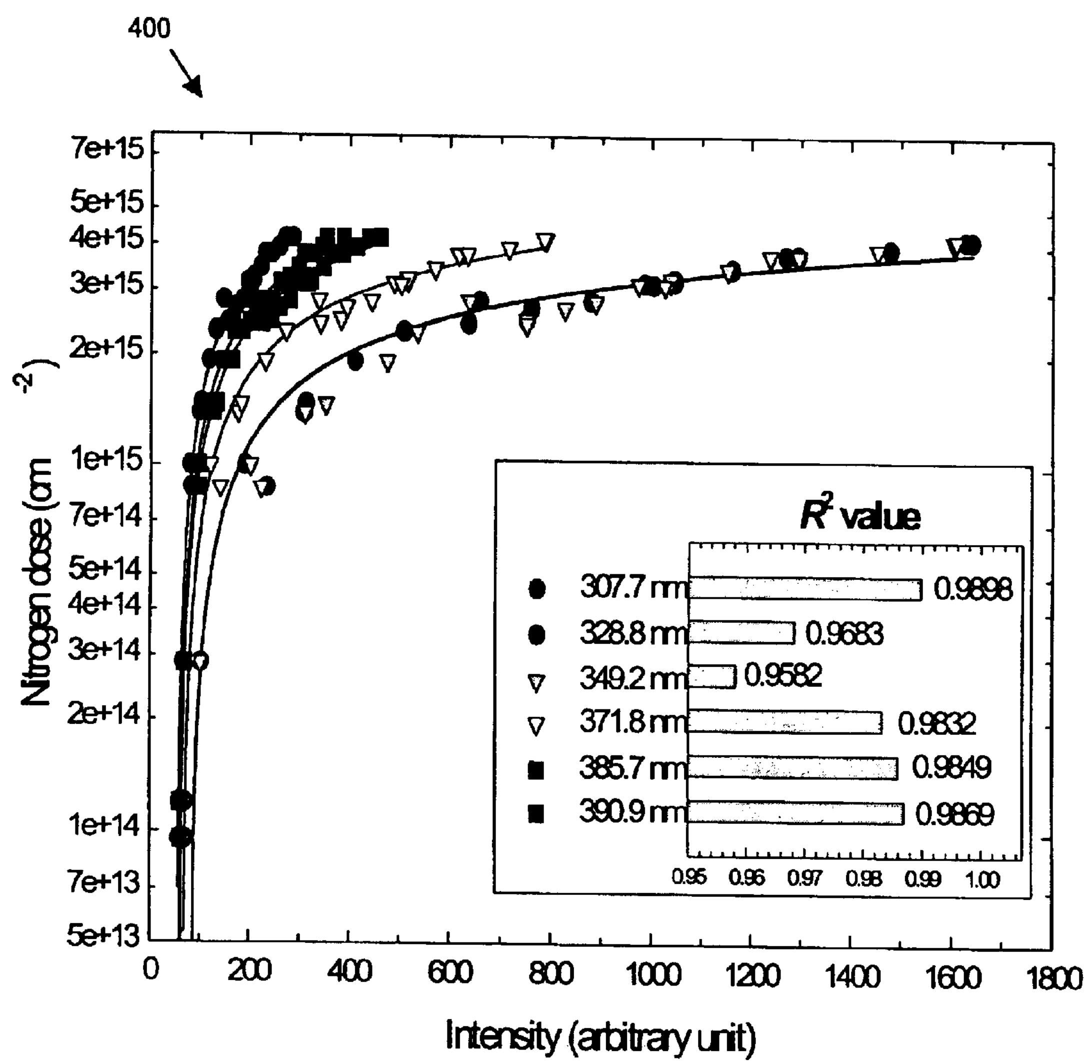
FIG. 4 illustrates a graph demonstrating the correspondence of component concentration to wavelength specific intensities according to aspects of the present disclosure.

A correlation may be found between nitrogen concentration in the nitrided gate oxide and these peak intensities. Moreover, this correlation becomes stronger at shorter optical wavelengths when compared to longer optical wavelengths. For example, referring to FIG. 4, illustrated is a graph 400 showing the correlation of the exemplary data shown in FIG. 3. The x-axis in the graph 400 represents intensities (arbitrary units) at various wavelengths, and the y-axis represents nitrogen concentrations corresponding to the intensities. In the particular embodiment shown, correlations ($R^2$) ranging between about 0.9582 and about 0.9898 may be found for wavelengths ranging between about 307.7 nm and about 390.9 run. Generally, wavelengths ranging between about 290 nm and about 400 nm may be employed with the methods described herein, although other wavelengths also may be useful, such as in the detection of component concentrations other than nitrogen in features other than gate oxides.

Obviously, it may be desired to select the wavelength providing the strongest correlation between intensity and nitrogen concentration for a particular application. Thus, in one embodiment, the intensity at a wavelength of about 308 nm may be employed to predict, determine or monitor the nitrogen concentration of the gate oxide 210 shown in FIG. 2 before, during or after its formation. In another embodiment, the intensity at a wavelength of about 329 nm may be employed. In another embodiment, the intensity at multiple wavelengths may be employed.

Figure 5:
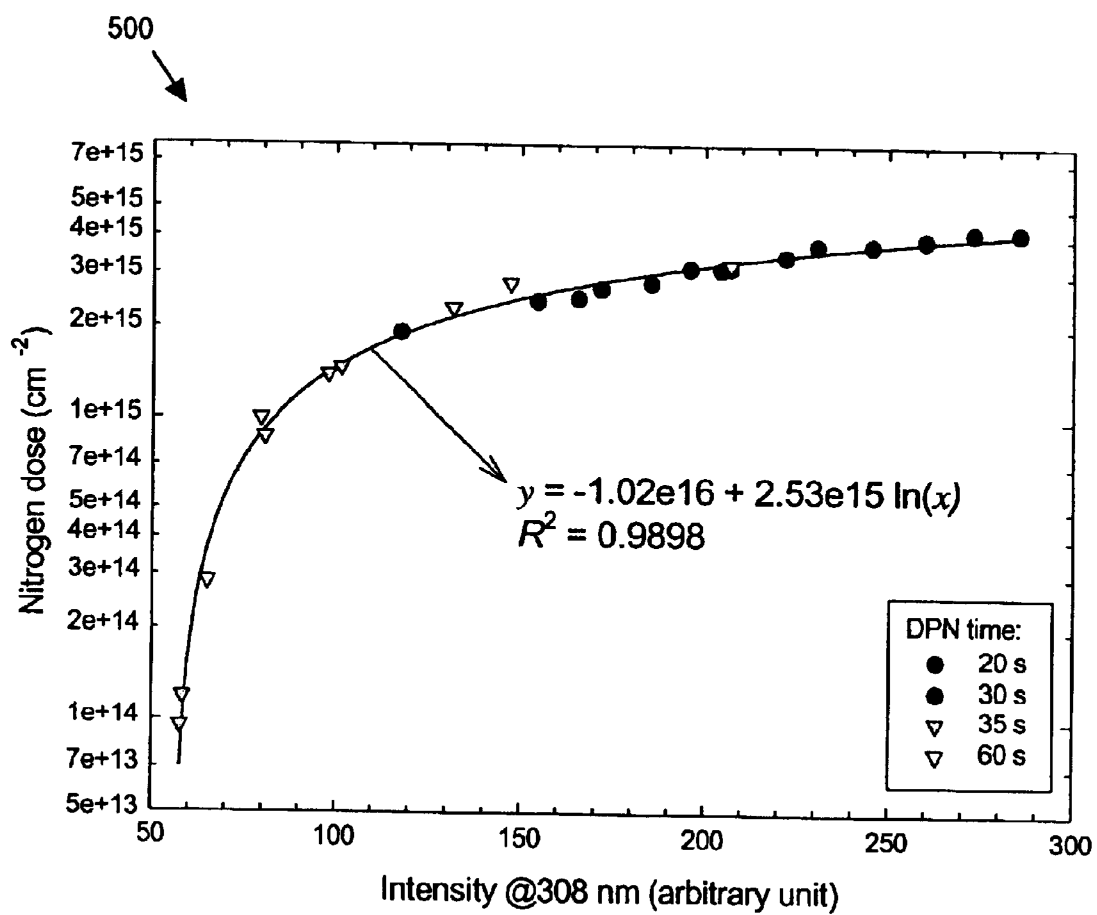
FIG. 5 illustrates a graph demonstrating one embodiment of an empirical correspondence of component concentration to intensity at a specific wavelength according to aspects of the present disclosure.

FIG. 5 illustrates one embodiment employed to determine the component concentration based on the intensity of a selected wavelength, although other methods also may be employed. Although many wavelengths may provide acceptable correlation, FIG. 5 illustrates a graph 500 demonstrating the correlation of intensity (arbitrary units) at a wavelength of about 308 nm to nitrogen concentration ($cm^{-2}$). In the particular embodiment shown in FIG. 5, an empirical method has been employed to correlate the nitrogen concentrations and intensities. Specifically, the relation may be approximated by the equation:

$$y=-1.02E16+2.53E15\ \ln \qquad (x)$$

wherein x represents intensity and y is the nitrogen concentration corresponding to the intensity. Such an empirical method may provide a correlation of about 0.9898.

Thus, as the gate oxide 210 shown in FIG. 2 is being formed, optical radiant energy generated by the plasma nitridation process in which gate oxide 210 is nitrided may be analyzed to monitor the intensity of signals at a wavelength of about 308 nm, and the above equation may be used to determine the nitrogen concentration in the gate oxide 210. For example, as the intensity reaches about 100 (arbitrary units), the nitrogen concentration may be about 1.45E15 atoms/$cm^2$. Using different process parameters, the intensity of the 308 nm wavelength signal may increase to about 250, at which point the nitrogen concentration may be about 3.77E15 atoms/$cm^2$. In one embodiment, process parameters may be adjusted so that the nitrogen concentration reaches a preferred concentration of about 1 E14 to 5E15 atoms/$cm^2$.

Moreover, because the method may be performed without removing the wafer 110 from the process chamber, the method may be an in-situ method, thereby eliminating the damage potentially caused by removing the wafer 110 from the chamber and exposing the wafer 110 to air or another undesired ambient.

Generally, it appears that OES peak intensity is determined primarily by nontime process parameters, such as power and pressure. In other words, peak intensity does not appear to be a function of time, and therefore the nitrogen dose is not determined by time. Instead, the nitrogen dose is correlated to the peak intensity at the appropriate wavelength or wavelengths, which is determined by process power and pressure. Temperature also may be a parameter that can affect the peak intensity.

Figure 6:
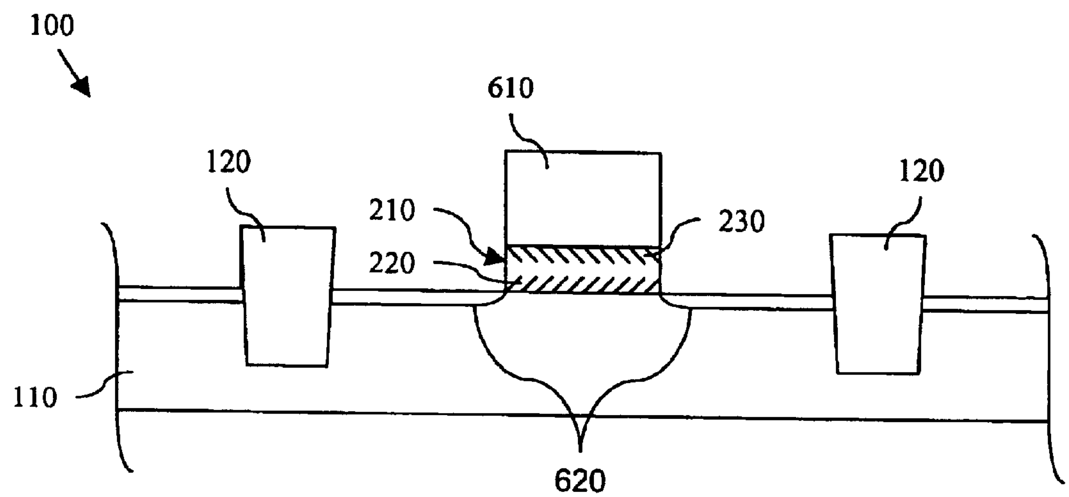
FIGS. 6 and 7 illustrate sectional views of the semiconductor device shown in FIGS. 1 and 2 in subsequent stages of manufacture according to aspects of the present disclosure.

Referring to FIG. 6, illustrated is a sectional view of the device 100 shown in FIG. 2 in a subsequent stage of manufacture. After forming the nitrided gate oxide 210 as described above, a gate electrode 610 may be formed over the gate oxide 210. Although shown as a single discrete feature, the gate electrode 610 may be formed in a number of ways. In one embodiment, the gate electrode 610 may include a laminar structure having a doped polysilicon layer over an un-doped polysilicon layer. The gate electrode 610 may also include a polycide structure having a silicide layer over a polysilicon layer.

The gate electrode 610 may be patterned, such as by anisotropic etching, or reactive ion etching (RIE), with a plasma containing a halogen or halogen compound. In one embodiment, the etching may employ HBr to take advantage of the relatively high silicon-to-gate oxide etch rate ratio that can be achieved with HBr. The incorporation of nitrogen into the gate oxide 210 as described above may also further protect the gate oxide 210 from etching by halogen based etchants such as HBr, thereby improving the effectiveness of the gate oxide 210 as an etch stop in the patterning process employed to define the gate electrode 610. In general, those skilled in the art are familiar with the myriad structures and methods which may be employed to form the gate electrode 610, such that processes, materials and structures other than those described above may also or alternatively be employed to form the gate electrode 610.

After patterning the gate electrode 610, the gate oxide 210 may be patterned by conventional or future-developed means employing the gate electrode 610 as a mask. Thereafter, lightly doped source/drain regions 620 may be conventionally formed, such as by ion implantation, employing the gate electrode 610 as a mask.

Figure 7:
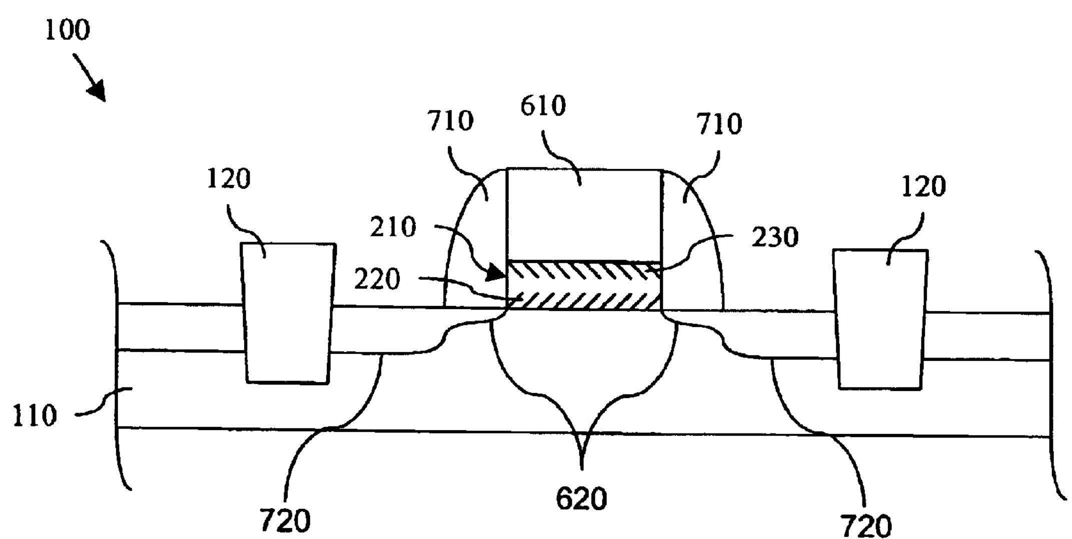

Referring to FIG. 7, illustrated is a sectional view of the device 100 shown in FIG. 6 in a subsequent stage of manufacture. In one embodiment, the device 100 shown in FIG. 7 may be substantially complete. After forming the source/drain regions 620, sidewall structures or spacers 710 may be formed on opposing sides of the gate electrode 610 and gate oxide 210. The spacers 710 may be of conventional materials and construction, such as blanket or selective deposition of $SiO_2$ or other dielectrics followed by an etch-back or other material removal process. Thereafter, heavily doped source/drain regions 720 may be conventionally formed, such as by ion implantation, employing the gate electrode 610 and spacers 710 as a mask.

Figure 8:
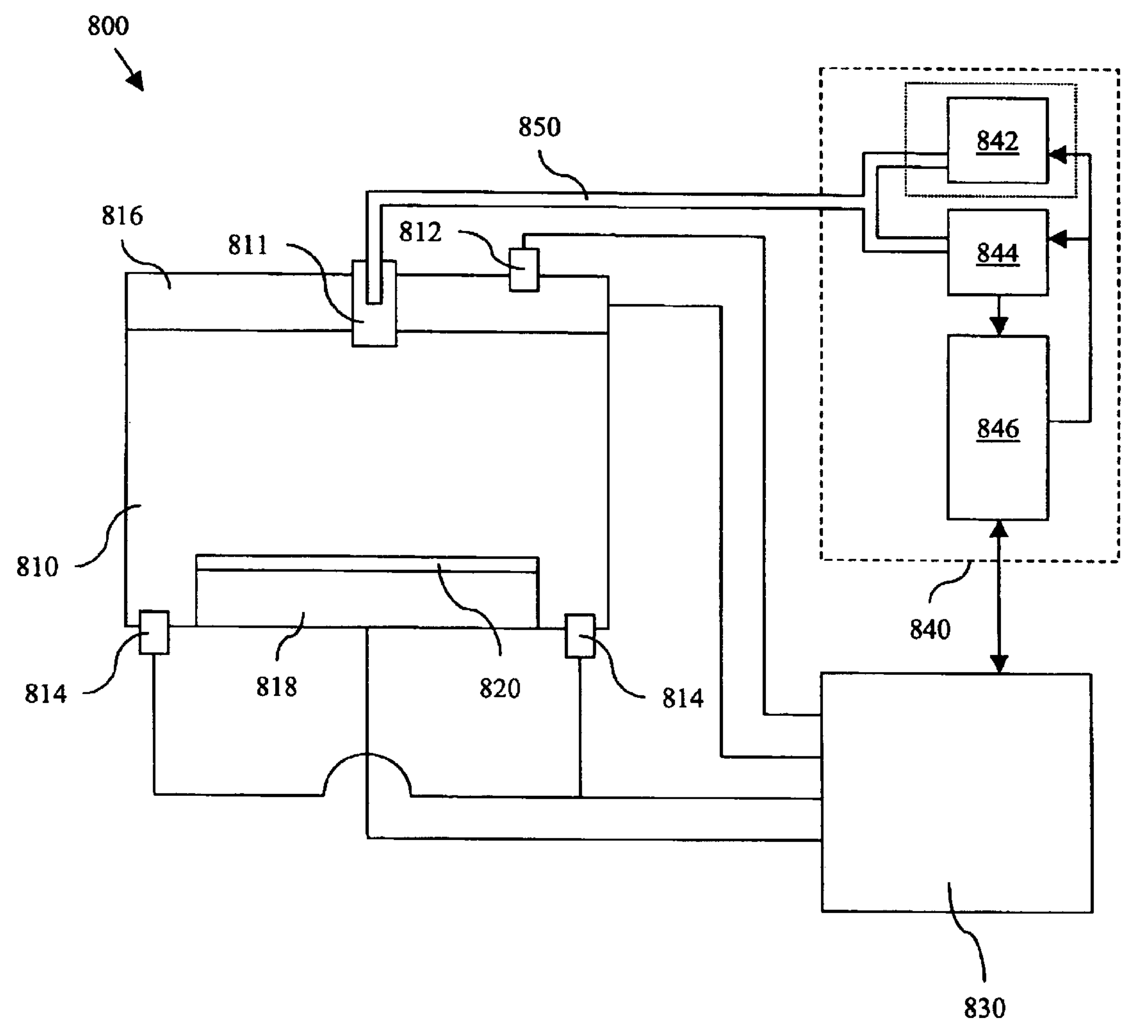
FIG. 8 illustrates a block-diagram of one embodiment of a plasma system constructed according to the aspects of the present disclosure.

Referring to FIG. 8, illustrated is a block diagram of one embodiment of a plasma system 800 for use in manufacturing a semiconductor device constructed according to the principles of the present disclosure. The system 800 may be one environment in which the manufacture of the device 100 shown in FIGS. 1, 2, 6 and 7 may be implemented.

The system 800 includes a processing chamber 810 which may include an optical port 811, gas input means 812, gas output means 814, a first electrode 816 and an opposing second electrode 818. The processing chamber 810 may be suitable to run vacuum processes, such as plasma nitridation, etching, sputtering, ion implantation or chemical vapor deposition (CVD) processes. In such embodiments, the processing chamber 810 may be a vacuum chamber, and a vacuum pump (not shown) may be connected to the gas output means 814. Alternatively, the processing chamber 810 may run processes such as atmospheric pressure CVD, wherein the processing chamber 810 may be held at about atmospheric pressure, possibly with a slight vacuum.

The optical port 811 may include a window through which optical signals may pass without substantial modification, such as one comprising optically transparent glass. For example, the optical port 811 may include at least one window or view port made of a material that is transparent for the wavelength of the radiation passing therethrough. The optical port 811 may also include focusing or diffusing means as known to those skilled in the art.

The gas input means 812 may include fluid/gas transfer ports and/or pumps for delivering a process gas or other process reactants to the processing chamber 810. Effluent from the processing chamber 810 is exhausted through the gas output means 814.

The second electrode 818 may include or be incorporated in a wafer support, such that a wafer 820 being processed may rest on or be coupled to the second electrode 818 between the first and second electrodes 816, 818. The processing chamber 810 may also include other features not described or illustrated. For example, the processing chamber 810 may also include temperature control means (e.g., a heater), process gas distribution means, radio frequency coils, etc.

The system 800 also includes a process control unit 830 electrically coupled to the gas input means 812 and gas output means 814 to control the pressure and contents of the processing chamber 810. The process control unit 830 may also be electrically coupled to the first and second electrodes 816, 818, such as for controlling electrical signals at the first and second electrodes 816, 818. For example, the process control unit 830 may provide electrical signals to the first and second electrodes 816, 818 as required for exciting the chamber contents, possibly for forming an etching or deposition plasma as known in the art. In one embodiment in which the system 800 may be employed for plasma etching or chemical vapor deposition (CVD), the signals provided by the process control unit 830 at the first and second electrodes 816, 818 may be RF signals. Of course, the present disclosure is not limited to such an embodiment.

The system 800 also includes a measurement and analysis unit 840 ("MA unit 840") electrically coupled to the process control unit 830. As such, the MA unit 840 may communicate with the process control unit 830, and may thereby trigger or control the modification of the process parameters based on analysis performed by the MA unit 840. For example, process parameters such as RF power, microwave power, chamber pressure, chamber temperature and processing time may be adjusted, possibly based on the component concentration of a feature being formed.

The MA unit 840 is also optically coupled to the process chamber 810 by an optical fiber 850, which may comprise a fiber bundle.

The MA unit 840 also includes an optical signal analyzer 844 configured to receive optical signals resulting from the irradiation reflected from the wafer 820. As shown in FIG. 8, such optical signals may propagate along the optical fiber 850 between the processing chamber 810 and the optical signal analyzer 844. The optical signal analyzer 844 may be configured to perform the analysis described above with respect to the prediction, detection or monitoring of a concentration of a component in a feature formed or being formed on the wafer 820, although additional or alternative analyses may be performed by the optical signal analyzer 844.

In an alternate embodiment, the MA unit 840 may include an optional light source 842 (such as a laser or bright white light source) coupled to the optical fiber 850 for irradiating chamber 810 or wafer 820. The light source 842 may emit one or both of a monochromatic (single wavelength) light, such as from a light-emitting diode, and polychromatic (multiple wavelength) white light.

The MA unit 840 also includes a management unit 846. The management unit 846 may be coupled to the optical signal analyzer 844 to facilitate the collection and analysis of the optical signals reflected from the wafer 820. For example, the management unit 846 may receive data from the optical signal analyzer 844, such as data indicating a change in the intensity or other optical characteristics of the plasma in the processing chamber 810. The management unit 846 also may control the operation of spectral analyzer 844. The management unit 846 also may be coupled to the process control unit 830 for assisting in the control of the process parameters, such as when a change in the process parameters may be modified based on a change in the characteristics of the plasma, as measured by the optical signal analyzer 844. In an alternate embodiment, the management unit 846 also may be coupled to light source 842 for controlling the irradiation of chamber 810 or wafer 820. One of skill in the art will understand that the various control mechanisms may be arranged in any number of ways and remain within the scope of the present invention. For example, all of the functions may be controlled by a single processor, or may be split up between different controllers.

Thus, the present disclosure presents the concept of determining a component concentration of a feature being formed on a substrate in which such determination may incorporate the optical characteristics of the plasma used during formation. Such a process allows prediction or determination of a concentration of nitrogen or other component in a gate oxide or other feature included in a MOSFET or other microelectronic device. Moreover, the component concentration detection processes described in the present disclosure may be in-situ or real-time processes. As such, the increased accuracy provided by the methods of the present disclosure may be attained with minimal or no impact to existing manufacturing time and costs. Furthermore, the processes of the present disclosure may be performed with existing manufacturing equipment and readily implemented into existing manufacturing procedures. The method and apparatus may also be adapted for use with many manufacturing processes, including other plasma and non-plasma processes.

Although the present disclosure describes several embodiments in detail, those skilled in the art should understand that they may make various changes, substitutions and alterations herein without departing from the spirit and scope of the disclosure.

What is claimed is:

1. A method of manufacturing a semiconductor device comprising the steps of:

forming a first multiplicity of semiconductor circuit features having a selected thickness;

providing a plasma chamber and an OES (Optical Emission Spectroscopy) for monitoring light emissions;

nitriding said multiplicity of semiconductor circuit features on said multiplicity of substrates in said chamber using a plasma;

monitoring the light emissions in said plasma chamber during said nitriding of said multiplicity of semiconductor features;

collecting intensity data representative of optical energy emitted at different wave lengths during said nitriding of said multiplicity of semiconductor features;

determining the peak intensity at different wavelengths of said monitored light emissions over a selected period of time reached at a multiplicity of settings of at least one selected parameter controlling the plasma generated in the chamber and the correlation between peak intensity level and the concentration level of a selected component in said semiconductor feature;

selecting a wave length of light having a strong correlation with the peak intensity level representative of a desired concentration level of said component in said feature of a semiconductor circuit and adjusting said at least one selected parameter controlling the plasma generated in a plasma chamber to a setting corresponding to said selected pea intensity level;

nitriding another circuit having said semiconductor features with said selected thickness and monitoring the intensity level of said selected wave length of light during said nitriding of said another circuit; and continuing nitriding said another circuit until said intensity level of light emissions at said selected wavelength stops increasing, the intensity level of which said selected wavelength stops increasing representing the peak intensity level.

2. The method as recited in claim 1 further comprising adjusting said parameters to achieve said component concentration at about 1E14 to 5E15 atoms/$cm^2$.

3. The method as recited in claim 1, wherein said parameters are selected from the group consisting of: RF power, microwave power, pressure, and temperature.

4. The method as recited in claim 1, wherein said semiconductor circuit feature is a gate oxide.

5. The method as recited in claim 4 wherein said component is nitrogen.

6. The method of claim 5, wherein said gate oxide feature of said semiconductor circuit is implanted with nitrogen ions ($N_2$+) and annealed prior to said step of plasma treating.

7. The method of claim 6 wherein said implantation dose is between about 1E14 atoms/$cm^2$ and about 1E15 atoms/$cm^2$.

8. The method of claim 7 wherein annealing of said gate oxide feature is at a temperature of between about 1000° C. and about 1050° C.

9. The method of claim 5 wherein said plasma treating is maintained for a period ranging between about 3 minutes and about 5 minutes.

10. The method of claim 5 wherein said plasma treating step comprises a gas flow rate of between about 600 SCCM and 3000 SCCM.

11. The method as recited in claim 1, wherein said selected wavelength is between about 290 nm and about 400 nm.

12. The method as recited in claim 11 wherein said selected wavelengths are between about 308 nm, and about 329 nm.

13. The method as recited in claim 1, wherein said component concentration is related to said peak intensity as estimated by the equation $y=-1.02E16+2.53E15 \ln(x)$, wherein x is said peak intensity and y is said component concentration.

14. The method as recited in claim 1 wherein said semiconductor circuit feature has a thickness ranging between about 13 Angstroms and about 17 Angstroms.

15. A method of manufacturing a semiconductor device comprising the steps of:

providing a plasma chamber and an (Optical Emission Spectroscopy) OES for monitoring light emissions;

monitoring the light emissions in said plasma chamber during plasma treatment of a multiplicity of semiconductor circuits having a feature with a selected thickness;

collecting intensity data representative of optical energy emitted at different wavelengths of light during the plasma treatment;

determining the peak intensity level of selected wavelengths of said monitored light emissions for a multiplicity of settings of at least one selected parameter controlling the plasma generated in the plasma chamber and the correlation between said peak intensity level and the concentration level of a selected component in said semiconductor feature;

selecting a wavelength of light having a correlation with the peak intensity level representative of a desired concentration level of said component in said feature of a semiconductor circuit, and adjusting said at least one parameter controlling the plasma generated in a plasma chamber to a setting corresponding to said determined selected peak intensity level;

plasma treating a semiconductor circuit in the process of being fabricated and having said feature with said selected thickness, and monitoring the intensity level of said selected wavelength of light during said plasma treatment; and continuing said plasma treatment of said semiconductor circuit until said intensity level of light emission at said selected wavelength reaches its peak intensity level and stops increasing.

16. The method as recited in claim 15 wherein said parameters are selected from the group consisting of: RF power, microwave power, pressure, and temperature.

17. The method of claim 15 wherein said selected wavelength is between about 100 nm and about 900 nm.

* * * * *